(12) United States Patent
Patten et al.

(10) Patent No.: US 8,631,687 B2
(45) Date of Patent: Jan. 21, 2014

(54) INDENTER ASSEMBLY

(75) Inventors: Justin D. Patten, Eden Prairie, MN (US); Christopher David Young, Shorewood, MN (US); Lucas Paul Keranen, Hutchinson, MN (US)

(73) Assignee: Hysitron, Inc., Minneapolis, MN (US)

( * ) Notice: Subject to any disclaimer, the term of this patent is extended or adjusted under 35 U.S.C. 154(b) by 174 days.

(21) Appl. No.: 13/090,036

(22) Filed: Apr. 19, 2011

(65) Prior Publication Data

US 2011/0252874 A1 Oct. 20, 2011

Related U.S. Application Data

(60) Provisional application No. 61/325,670, filed on Apr. 19, 2010.

(51) Int. Cl.
*G01N 3/48* (2006.01)

(52) U.S. Cl.
USPC .............................................. 73/81

(58) Field of Classification Search
USPC .............................................. 73/81
See application file for complete search history.

(56) References Cited

U.S. PATENT DOCUMENTS

| | | |
|---|---|---|
| 3,896,314 A | 7/1975 | Nukui et al. |
| 4,491,788 A | 1/1985 | Zandonatti |
| 4,992,660 A | 2/1991 | Kobayashi |
| 4,996,433 A | 2/1991 | Jones et al. |
| 5,367,171 A | 11/1994 | Aoyama et al. |
| 5,654,546 A | 8/1997 | Lindsay |
| 5,661,235 A * | 8/1997 | Bonin .............................. 73/105 |
| 5,731,587 A | 3/1998 | DiBattista et al. |
| 5,869,751 A * | 2/1999 | Bonin .............................. 73/105 |
| 6,339,958 B1 | 1/2002 | Tsui et al. |

(Continued)

FOREIGN PATENT DOCUMENTS

| | | |
|---|---|---|
| WO | WO-2008061224 | 5/2008 |
| WO | WO-2011066018 A1 | 6/2011 |

(Continued)

OTHER PUBLICATIONS

"U.S. Appl. No. 13/510,825, Non Final Office Action mailed Mar. 27, 2013", 14 pgs.

(Continued)

*Primary Examiner* — Lisa Caputo
*Assistant Examiner* — Jamel Williams
(74) *Attorney, Agent, or Firm* — Schwegman Lundberg & Woessner, P.A.; Thomas C. Obermark; Arlene Hornilla

(57) ABSTRACT

An indentation assembly for sub-micron testing includes an indentation tip and a tip holder coupled with the indentation tip. The tip holder includes a first thermal conductivity and a first coefficient of thermal expansion. A tip holder mount configured for coupling with a transducer and the tip holder, the tip holder mount having a second thermal conductivity greater than the first thermal conductivity, and the tip holder mount has a second coefficient of thermal expansion greater than the first coefficient of thermal expansion. The tip holder mount has a mount length, and the tip holder further has a tip holder length greater that the mount length. The tip holder remotely positions the tip holder mount relative to the indentation tip. The tip holder length, volume and the first thermal conductivity cooperate to throttle heat transfer through the tip holder prior to reaching the tip holder mount.

28 Claims, 13 Drawing Sheets

(56) References Cited

U.S. PATENT DOCUMENTS

| | | | |
|---|---|---|---|
| 6,495,838 | B1 | 12/2002 | Yaguchi et al. |
| 6,520,004 | B1 * | 2/2003 | Lin .................................. 73/81 |
| 7,451,636 | B2 | 11/2008 | Bradshaw et al. |
| 7,685,868 | B2 * | 3/2010 | Woirgard et al. ................. 73/81 |
| 2002/0110177 | A1 | 8/2002 | Nakayama et al. |
| 2006/0025002 | A1 | 2/2006 | Zhang et al. |
| 2007/0278420 | A1 | 12/2007 | Molhave |
| 2008/0092938 | A1 | 4/2008 | Majumdar et al. |
| 2008/0276727 | A1 | 11/2008 | Enoksson et al. |
| 2009/0111701 | A1 | 4/2009 | Ahn et al. |
| 2009/0120172 | A1 | 5/2009 | Bradshaw et al. |
| 2009/0194689 | A1 | 8/2009 | Abramson et al. |
| 2010/0095780 | A1 | 4/2010 | Oh et al. |
| 2010/0132441 | A1 | 6/2010 | Oh et al. |
| 2010/0180356 | A1 | 7/2010 | Bonilla et al. |
| 2010/0186520 | A1 | 7/2010 | Wheeler, IV et al. |
| 2010/0212411 | A1 | 8/2010 | Passilly et al. |
| 2010/0294147 | A1 | 11/2010 | Loiret-Bernal et al. |
| 2011/0107472 | A1 | 5/2011 | Han et al. |
| 2011/0152724 | A1 | 6/2011 | Hansma et al. |
| 2012/0292528 | A1 | 11/2012 | Oh et al. |

FOREIGN PATENT DOCUMENTS

| | | | |
|---|---|---|---|
| WO | WO-2013074623 | A1 | 5/2013 |
| WO | WO-2013082145 | A1 | 6/2013 |
| WO | WO-2013082148 | A1 | 6/2013 |

OTHER PUBLICATIONS

"International Application Serial No. PCT/US2010/046865, International Preliminary Report on Patentability mailed May 30, 2012", 10 pgs.

"International Application Serial No. PCT/US2010/046865, Search Report mailed Oct. 28, 2010", 2 pgs.

"International Application Serial No. PCT/US2010/046865, Written Opinion mailed Oct. 28, 2010", 8 pgs.

"International Application Serial No. PCT/US2012/065009, International Search Report mailed Jan. 25, 2013", 2 pgs.

"International Application Serial No. PCT/US2012/065009, Written Opinion mailed Jan. 25, 2013", 5 pgs.

"International Application Serial No. PCT/US2012/066842, International Search Report mailed Feb. 7, 2013", 2 pgs.

"International Application Serial No. PCT/US2012/066842, Written Opinion mailed Feb. 7, 2013", 8 pgs.

"International Application Serial No. PCT/US2012/066846, International Search Report mailed Feb. 6, 2013", 2 pgs.

"International Application Serial No. PCT/US2012/066846, Written Opinion mailed Feb. 6, 2013", 8 pgs.

"International Application Serial No. PCT/US2013/031650, International Search Report mailed May 31, 2013", 2 pgs.

"International Application Serial No. PCT/US2013/031650, Written Opinion mailed May 31, 2013", 4 pgs.

Allard, L. F., et al., "A New Paradigm for Ultra-High-Resolution Imaging at Elevated Temperatures", Microscopy and Microanalysis, 14(Supp. S2), (2008), 792-793.

Briceno, M., et al., "In-situ TEM Observations on the Sintering Process of Colloidal Gold Using an Ultra-fast Heating Stage", Microscopy and Microanalysis, 14(Suppl 2), (2008), 1336-1337.

Damiano, John, et al., "A MEMS-based Technology Platform for in-situ TEM Heating Studies", Microscopy and Microanalysis, 14(Suppl 2), (2008), 1332-1333.

Eakins, D. E., et al., "An in situ TEM study of phase formation in gold-aluminum couples", Journal of Materials Science, 39, (2004), 165-171.

Kamino, T., et al., "A newly developed high resolution hot stage and its application to materials characterization", Microsc. Microanal. Microstruct., 4, (1993), 127-135.

Kamino, T., et al., "In-situ high-resolution electron microscopy study on a surface reconstruction of Au-deposited Si at very high temperatures", Philosophical Magazine A, 75(1), (1997), 105-114.

Min, K.-H., et al., "Crystallization behaviour of ALD-$Ta_2O_5$ thin films: the application of in-situ TEM", Philosophical Magazine, 85(18), (Jun. 21, 2005), 2049-2063.

Saka, H., "In situ observation of solid-liquid interfaces by transmission electron microscopy", J. Mater. Res., 20(7), (Jul., 2005), 1629-1640.

Saka, H., "In-situ TEM observation of transformation of dislocations from shuffle to glide sets in Si under supersaturation of interstitials", Philosophical Magazine, 86(29-31), (Oct.-Nov. 2006), 4841-4850.

Tsukimoto, S., et al., "In situ high resolution electron microscopy/ electron energy loss spectroscopy observation of wetting of a Si surface by molten Al", Journal of Microscopy, 203(Pt 1), (Jul., 2001), 17-21.

Wu, Yiying, et al., "Direct Observation of Vapor—Liquid—Solid Nanowire Growth", J. Am. Chem. Soc., 123, (Mar. 13, 2001), 3165-3166.

"U.S. Appl. No. 13/510,825, Final Office Action mailed Aug. 27, 2013", 26 pgs.

* cited by examiner

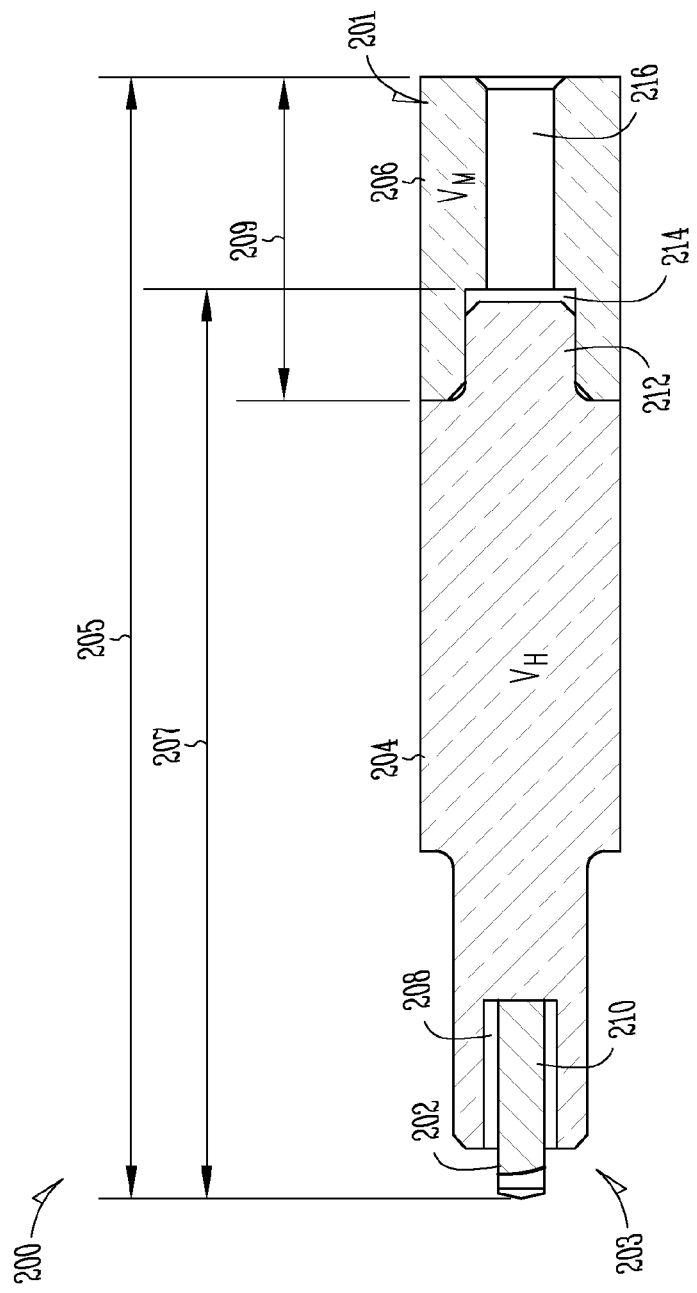
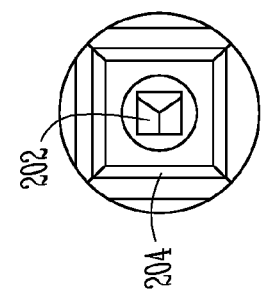
Fig.2B
Fig.2C

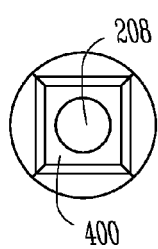 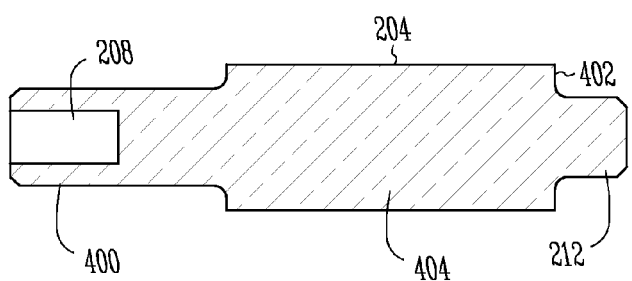 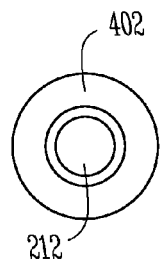
*Fig. 4D*  *Fig. 4C*  *Fig. 4E*
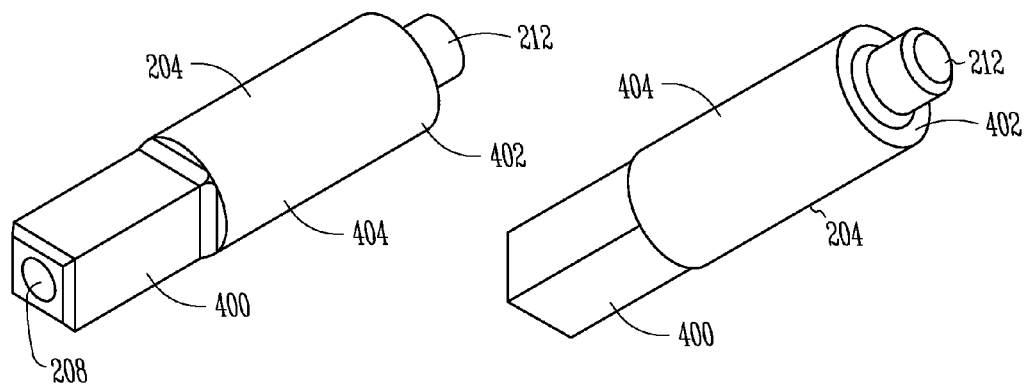
*Fig. 4A*  *Fig. 4B*

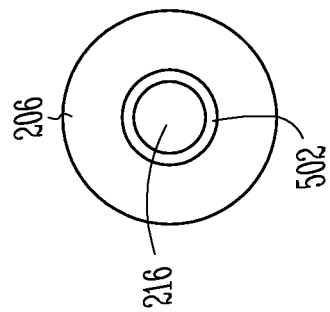
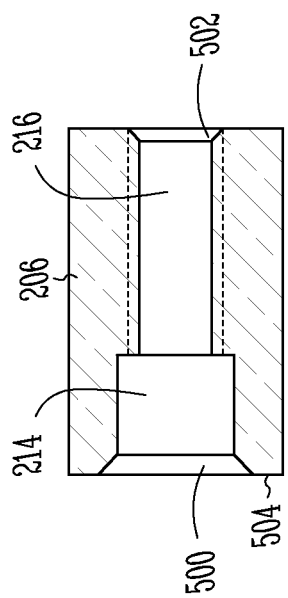
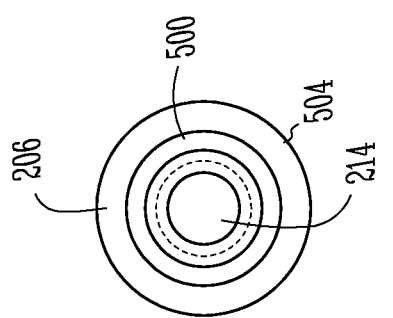

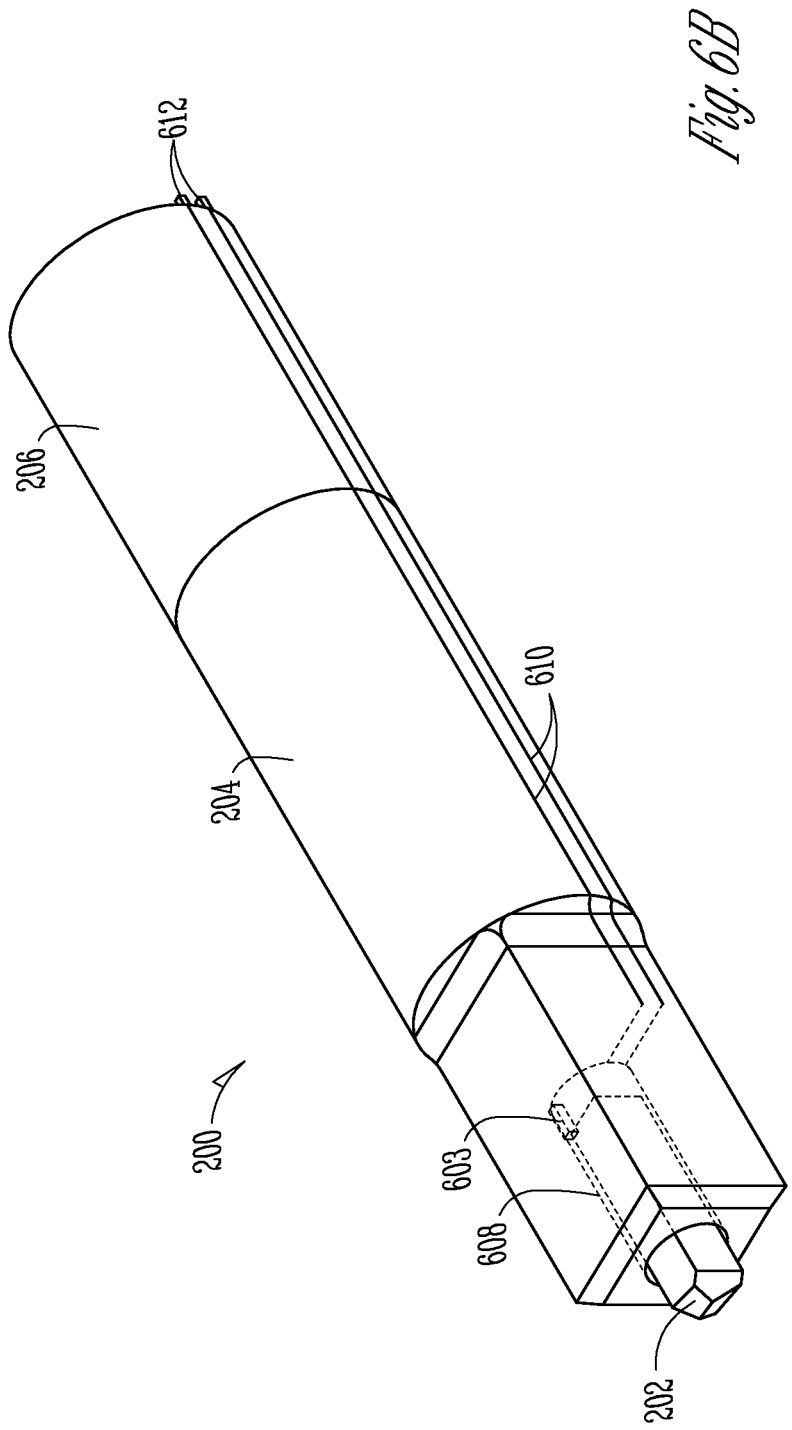

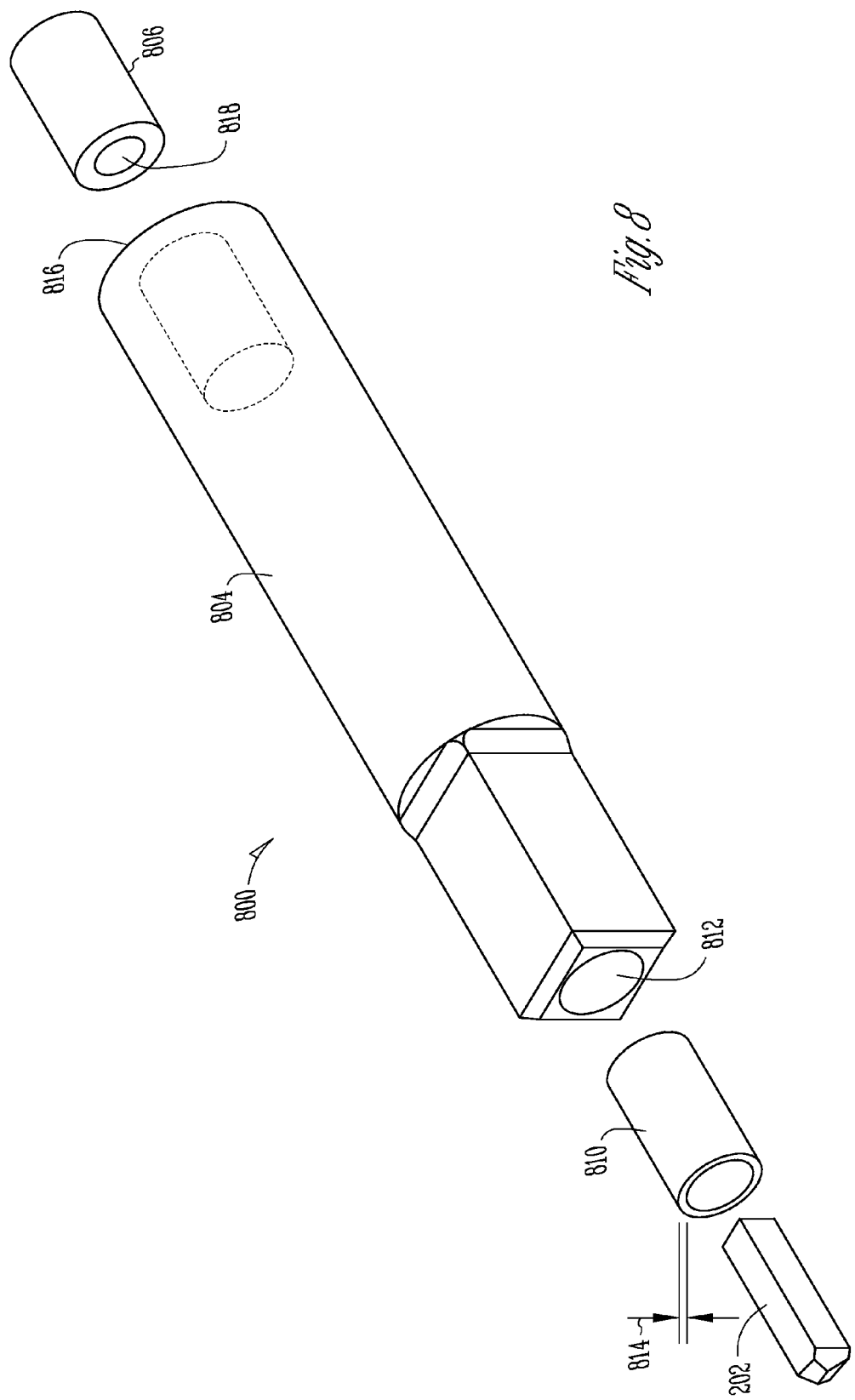

INDENTER ASSEMBLY

FIELD

Sub-micron scale mechanical testing.

BACKGROUND

Nanoindentation is a method to quantitatively measure a sample's mechanical properties, such as elastic modulus and hardness, for example, using a small force and a high resolution displacement sensor. Typically, a force employed in nanoindentation is less than 10 mN, with a typical displacement range being smaller than 10 µm, and with a noise level typically being better than 1 nm rms. In nanoindentation, a nanoindenter capable of determining the loading force and displacement is used. The force and displacement data are used to determine a sample's mechanical properties. In some examples, for sample property estimation a nanoindenter is integrated with a characterized tip which has known geometry and known mechanical properties.

One of the emerging nanoindentation applications is quantitative transmission electron microscopy (TEM) in-situ mechanical testing. This testing method enables monitoring of the deformation of a sample in real time while measuring the quantitative mechanical data. Coupling a nanomechanical system with TEM imaging allows researchers to determine certain material parameters such as variations in chemical composition or the presence of pre-existing defects in the specimen. In addition to imaging, selected-area diffraction can be used to determine sample orientation and loading direction. Moreover, with in-situ mechanical testing, the deformation can be viewed in real-time rather than "post mortem". Performing TEM in-situ nanomechanical testing can provide unambiguous differentiation between the many possible causes of force or displacement transients which may include dislocation bursts, phase transformations, shear banding or fracture onset while minimizing the effects of elastic recovery of the material surrounding the indentation.

Nanomechanical testing at elevated temperature is an important part of material characterization for materials having phase changes or variant mechanical properties as the temperature increases. Some of the applications of the high temperature nanomechanical test are glass transition temperature identification of polymeric and rubber materials, phase transformations of low temperature metals and shape memory alloys, study of biological samples at body temperature, simulated and accelerated thermal aging studies, accelerated material creep studies, and time-temperature-superposition curve plotting of polymers.

IN THE FIGURES

FIG. 2B is a cross-sectional side view of the indentation assembly shown in FIG. 2A.

FIG. 2C is a front elevational view of the indentation assembly shown in FIG. 2A.

Figure 3A:
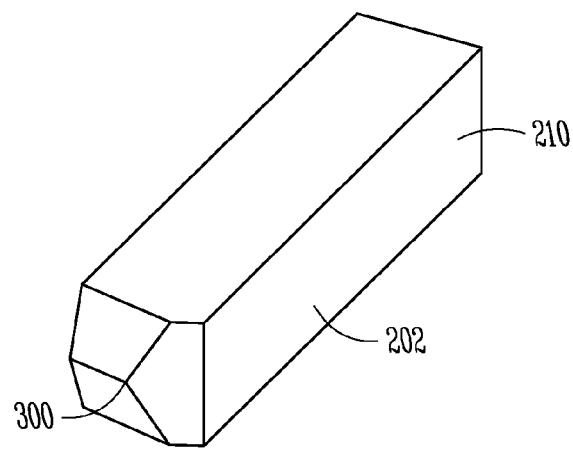
FIG. 3A is a perspective view of one example of an indentation tip.
Figure 3B:
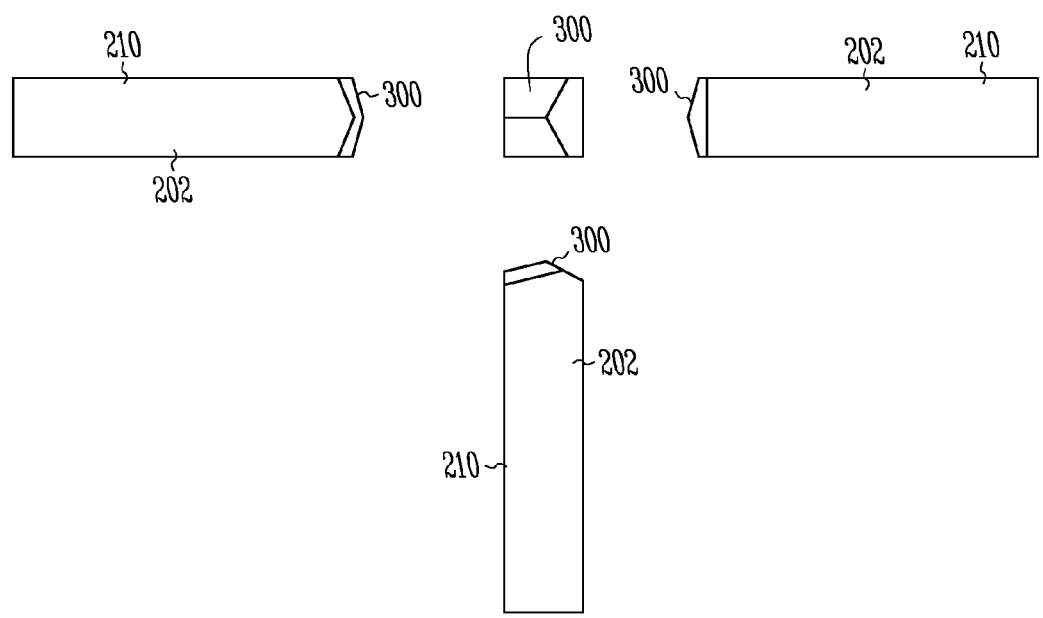

FIG. 3B includes multiple views of the indentation tip shown in FIG. 3A.

FIG. 4A is a front perspective view of one example of a tip holder.

FIG. 4B is a rear perspective view of the tip holder shown in FIG. 4A.

FIG. 4C is a cross-sectional side view of the tip holder shown in FIG. 4A.

FIG. 4D is a front elevational view of the tip holder shown in FIG. 4A.

FIG. 4E is a rear elevational view of the tip holder shown in FIG. 4A.

Figure 5A:
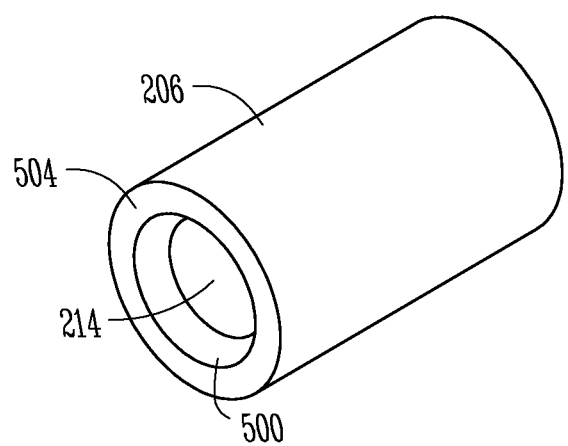

FIG. 5A is a front perspective view of one example of a tip holder mount.

Figure 5B:
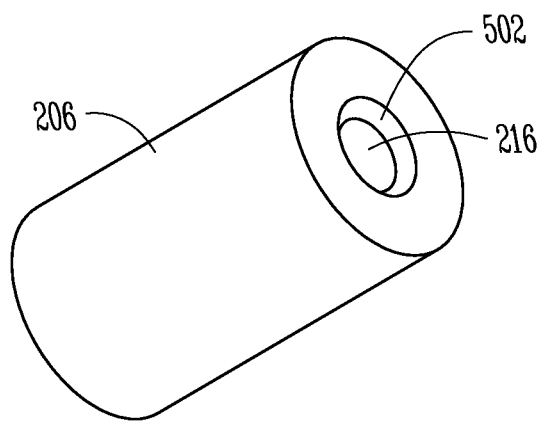

FIG. 5B is a rear perspective view of the tip holder shown in FIG. 5A.

FIG. 5C is a cross-sectional side view of the tip holder shown in FIG. 5A.

FIG. 5D is a front elevational view of the tip holder shown in FIG. 5A.

FIG. 5E is a rear elevational view of the tip holder shown in FIG. 5A.

Figure 6A:
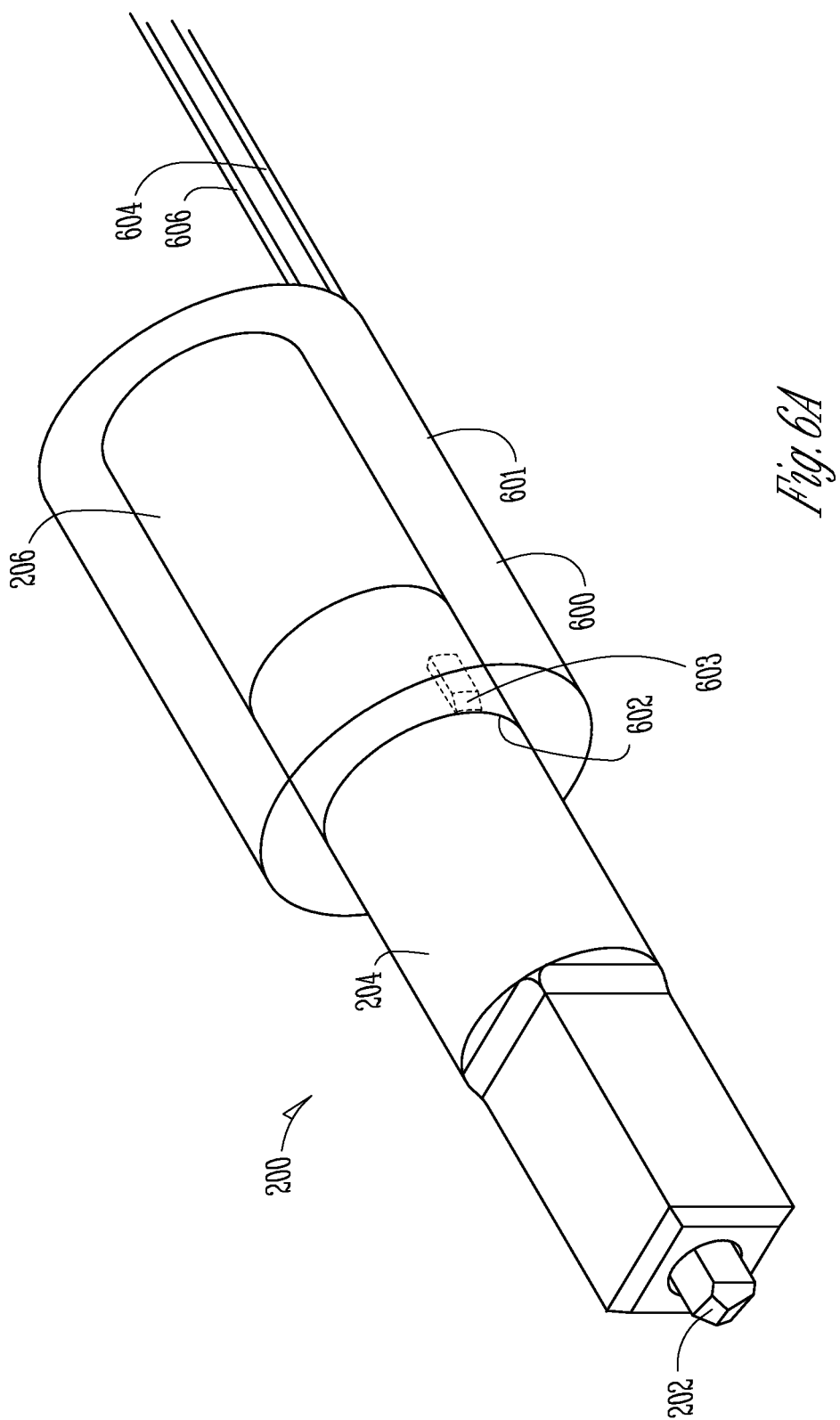

FIG. 6A is a perspective view of the indenter assembly shown in FIG. 2 coupled with a thermal shield.

FIG. 6B is a perspective view of the indenter assembly shown in FIG. 2 coupled with an heat exchanger.

Figure 6C:
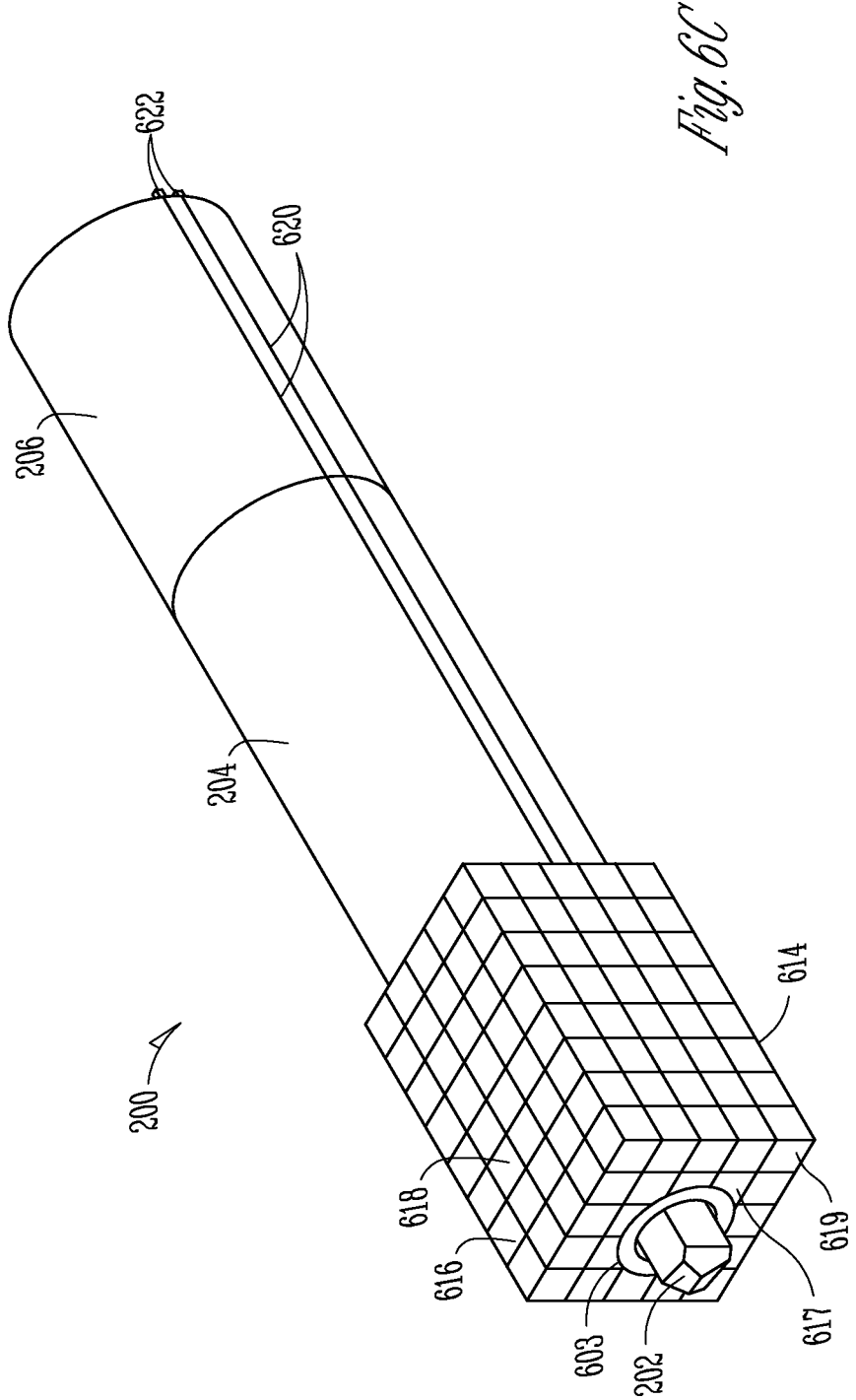

FIG. 6C is a perspective view of the indenter assembly shown in FIG. 2 coupled with a Peltier heat exchanger.

Figure 7A:
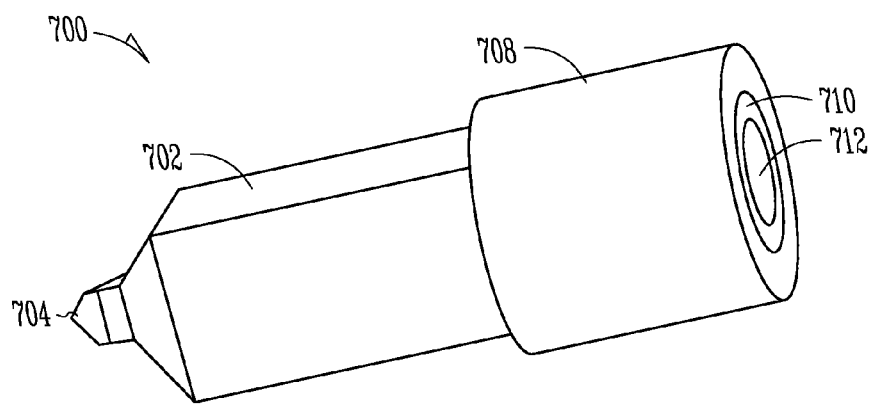

FIG. 7A is a perspective view of another example of an indenter assembly.

Figure 7B:
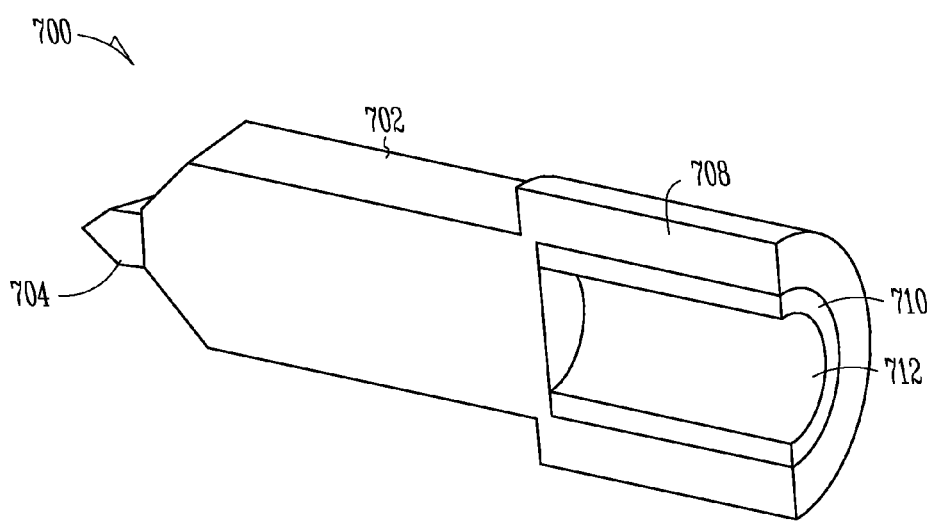

FIG. 7B is a perspective cross-sectional view of the indenter assembly shown in FIG. 7A.

FIG. 8 is an exploded view of yet another example of an indenter assembly.

Figure 9:
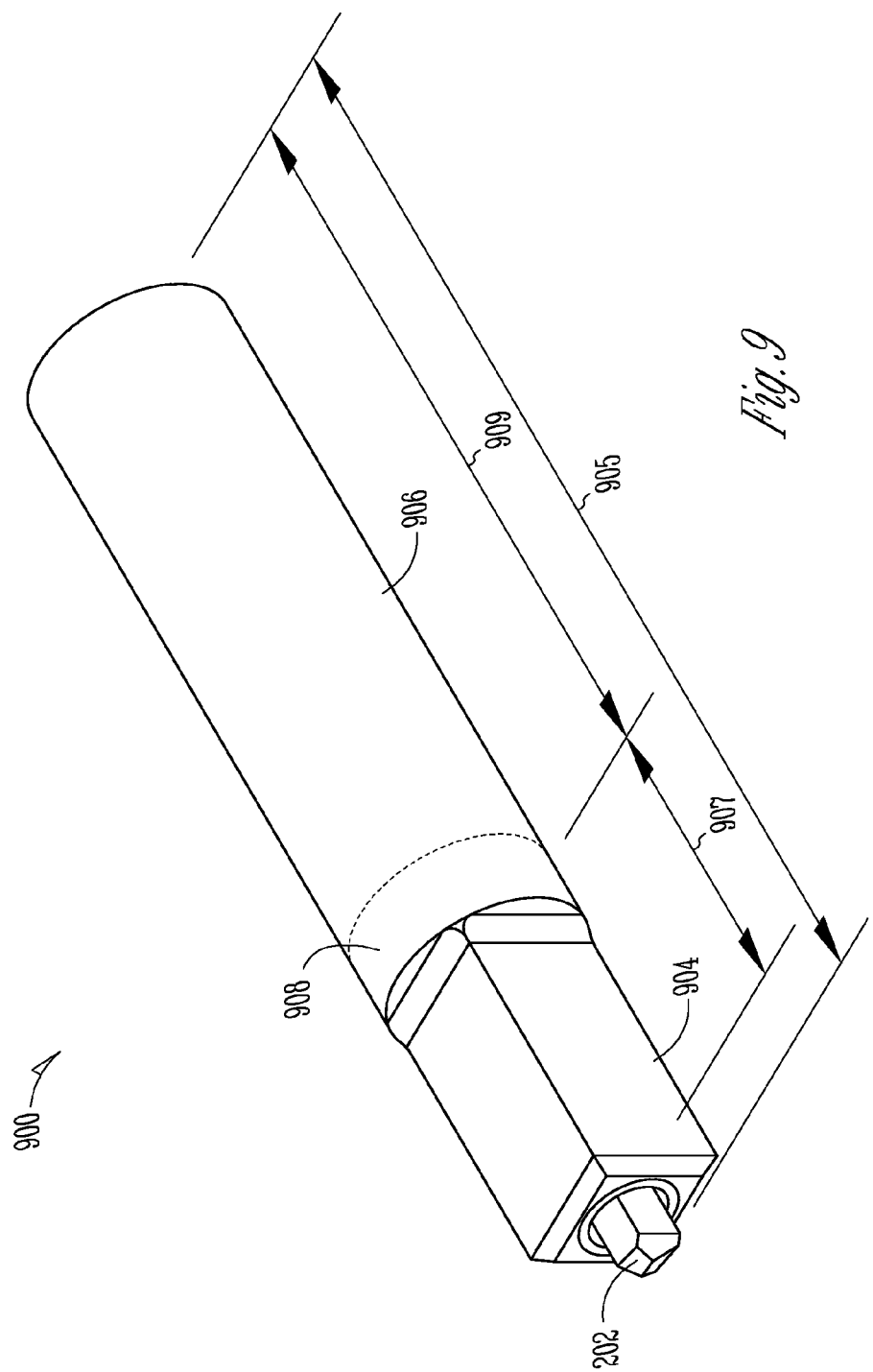

FIG. 9 is a perspective view of still another example of an indenter assembly including a tip holder extending along a portion of the indentation assembly.

DESCRIPTION

In the following detailed description, reference is made to the accompanying drawings which form a part hereof, and in which is shown by way of illustration how specific embodiments of the present disclosure may be practiced. In this regard, directional terminology, such as "top," "bottom," "front," "back," "leading," "trailing," etc., is used with reference to the orientation of the Figure(s) being described. Because components of embodiments of the present invention can be positioned in a number of different orientations, the directional terminology is used for purposes of illustration and is in no way limiting. These embodiments are described in sufficient detail to enable those skilled in the art to practice aspects of this disclosure, and it is to be understood that other embodiments may be utilized and that structural changes may be made without departing from the scope of the present disclosure. Therefore, the following detailed description is not to be taken in a limiting sense, and the scope of the present disclosure is defined by the appended claims and their equivalents.

According to embodiments described herein, a system and method are provided for mechanically testing small test subjects at both the nano and micro scales (i.e., sub-micron scale), including, but not limited to, nanostructures, thin films and the like. Such testing is performed, in one example, to determine the mechanical properties of the materials composing the subjects. According to examples described herein, a system and method are provided for mechanically testing small test subjects at both the nano and micro scales (i.e., sub-micron scale), including, but not limited to, nanostructures, thin films, metals, composites, ceramics, MEMS, polymers and the like. Such testing is performed, in one example, to determine the mechanical properties of the materials composing the subjects. Mechanical testing may include, but is not limited to, indentation, scratch testing, delamination force testing and the like with forces of around 10 mN or more (including Newton level forces at nanometer scale) and 10 N or more (at micron scale).

Figure 1:
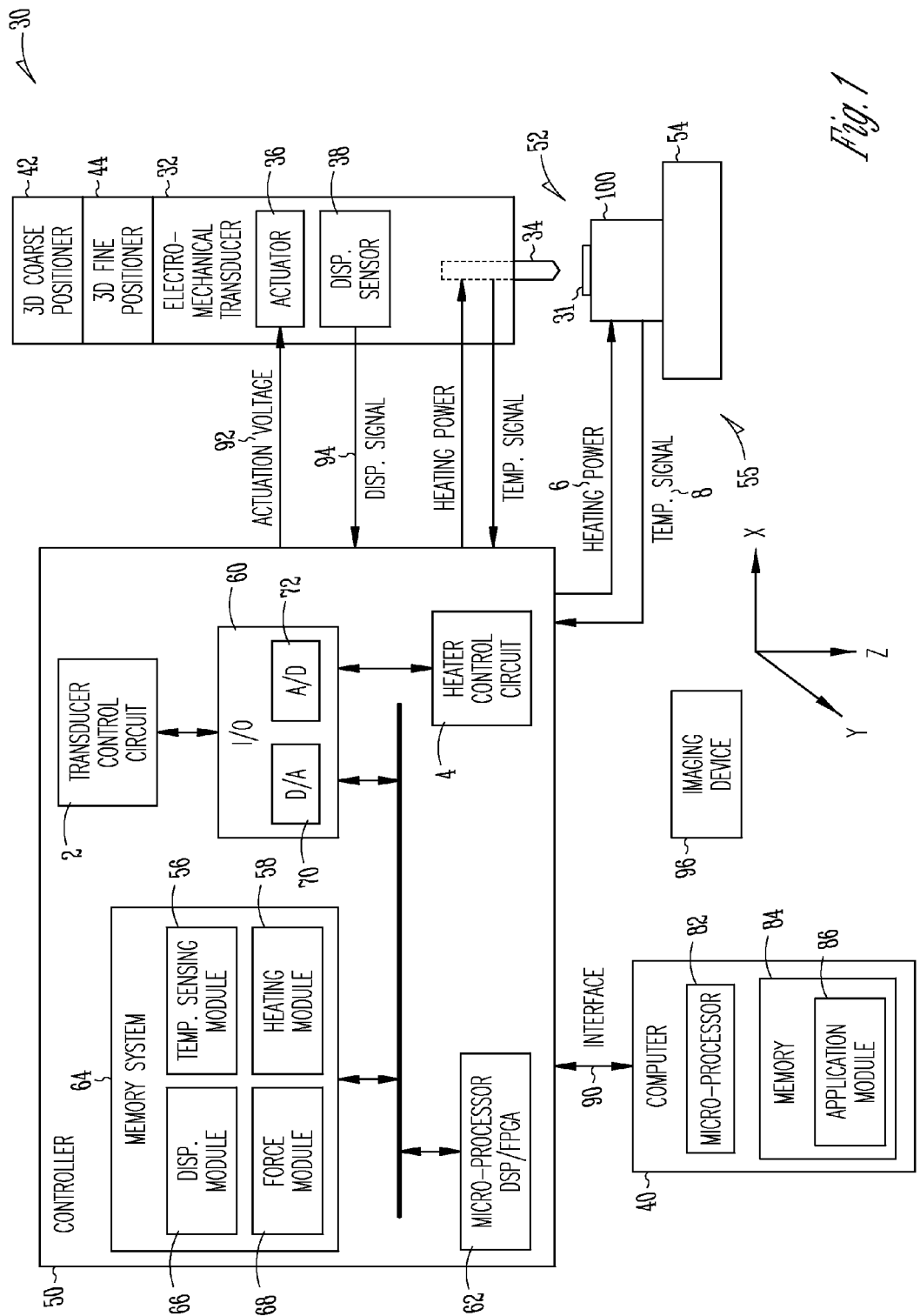
FIG. 1 is a block diagram showing one example of a sub-micron test system.

FIG. 1 is a schematic block diagram illustrating an example of a nanomechanical test system 30 employing a heater 100 (e.g., a MEMS heater, resistive heater, Peltier device and the like) for heating and sensing the temperature of a small test sample 31. In addition to the heater 100, the nanomechanical test system 30 (e.g., sub-micron) includes an electro-mechanical (EM including electrostatic and electromagnetic) transducer 32 having a displaceable probe 34, an actuator 36 to displace the probe 34, a displacement sensor 38, a computer 40, a coarse positioner 42, a fine positioner 44, and a controller 50. The EM transducer 32 includes, but is not limited to, indentation, compression, tensile, fatigue, tribology, fracture instruments and the like.

The nanomechanical test system 30 further includes a test subject holder 55 including a sample stage 52 and having a base portion 54 (a holder base). The heater 100 is positioned on the sample stage 52 (e.g., within or along the subject holder), and the holder is detachably mounted to the nanomechanical test system 30. According to one embodiment, and described in greater detail below, the heater 100 is micromachined or MEMS based so as to fit into a small, restricted space such as for in-situ nanomechanical testing application within a quantitative transmission electron microscope (TEM), for example.

According to one embodiment, the controller 50 includes an input/output module 60, a transducer control circuit 2, a heater control circuit 4, a processor 62, such as microprocessor or digital signal processor (DSP) and/or field programmable gate array (FPGA), for example, and a memory system 64. According to one embodiment, the memory system 64 includes a displacement module 66, a force module 68, a temperature sensing module 56, and a heating module 58. According to another embodiment, the input/output module 60 further includes a D/A converter 70, and an A/D converter 72.

In one example, the computer 40 includes a processor 82 and a memory system 84 that stores an application module 86. The computer 40 may access and communicate with the controller 50 via an interface 90 (e.g. a USB interface). FIG. 1 shows the computer 40 and controller 50 as separate entities. In other examples, computer 40 and controller 50 are combined as part of a single processing and control system.

According to one embodiment, the application module 86, displacement module 66, and force module 68 each include instructions respectively stored in memories 64 and 84 and which are accessible and executable by processor 62. Memories 64 and 84 include, but are not limited to, any number of volatile or non-volatile storage devices such as RAM, hard disk drives, CD-ROM drives, DVD drives and the like. In other embodiments, the displacement module 66, force module 68, temperature sensing module 56, and heating module 58 include any combination of hardware and software components configured to perform functions described herein. The software component of the displacement module 66 and the force module 68, the temperature sensing module 56, and the heating module 58 are each stored on a medium separate from the processing system 62 prior to being stored in memory system 64, in one example. Examples of such media include a hard disk drive, a compact disc (e.g. a CD-ROM, CD-R, or CD-RW), and a digital video disc (e.g. a DVD, DVD-R, and DVD-RW), for example.

According to one embodiment, the coarse positioner 42 and the fine positioner 44 enable 3-dimensional positioning (i.e. x-, y-, and z-axes in FIG. 1) of the EM transducer 32 and displaceable probe 34 in the millimeter range with a sub-nanometer resolution. According to one embodiment, final positioning and movement of the displaceable probe 34 is performed by the actuator 36 via the application module 86 on the computer 40 and the controller 50. According to one embodiment, the controller 50 is configured to control and monitor the movement of displaceable probe 34 and to provide data representative of a displacement of the displaceable probe 34 (from the displacement sensor 38) to the computer 40 through the interface 90. According to one embodiment, controller 50 is configured to determine and adjust a force applied to the test sample 31 by the displaceable probe 34.

According to one embodiment, the controller 50 is configured to control and monitor the temperature of the heater 100 and the test subject 31 and to provide data representative of a temperature of the heater 100 and the test subject 31 to the computer 40 via interface 90. In one example, the controller 50 is configured to determine and adjust a heating power 6 applied to the heater 100 and the test subject 31 to achieve a desired test subject temperature (and heater temperature) for testing and observation of the test subject In operation, a user can program the controller 50 with the computer 40 through the application module 86. According to one embodiment, the controller 50, through the force module 68, provides an input or force signal 92 to the actuator 36 representative of a desired force for application to the test sample 31 by the displaceable probe 34. In response to the input actuation force signal 92, the actuator 36 drives the displaceable probe 34 toward the sample stage 52 (e.g. along the z-axis in FIG. 1). The displaceable probe 34 contacts and applies the desired force to the test subject 31. The D/A converter 70 converts the input or force signal provided by the force module 68 from digital to analog form which, in turn, is amplified to generate the actuation force 92 by transducer control circuit 2 as provided to actuator 36.

The displacement sensor 38 comprises a transducer (e.g. a capacitive transducer) which detects movement of displaceable probe 34 at least along the z-axis, and provides a displacement signal 94 to controller 50 representing measurement of the movement of the displaceable probe 34. In other embodiments, in addition to movement along the z-axis, the displacement sensor 38 detects and provides indication of other types of movement of displaceable probe 34, such as displacement along the x- and/or y-axes or rotational movement about the x- and/or y-axes. The transducer control circuit 2 conditions the displacement signal 94 from the displacement sensor 38 and sends the displacement signal 94 to the A/D converter 72. The A/D converter 72 converts the displacement signal 94 from an analog form, as received from the transducer control circuit 2, to a digital form for processing by the displacement module 66. The displacement module 66, according to one embodiment, communicates measurement of the movement of the displaceable probe 34 to the force module 68 (e.g. for force calculations) and computer 40 (via interface 90).

According to one embodiment, controller 50 is further configured to control movement or displacement of displaceable probe 34 in the x- and y-directions relative to sample stage 52, such as by moving EM transducer 32 relative to sample stage 52 or by moving sample stage 52 relative to EM transducer 32. According to one embodiment, the nanomechanical test system 30 further includes an imaging device 96 comprising an instrument/device such as an electron microscope, an optical microscope, or a scanning probe microscope (SPM) configured to provide images of a test sample 31 mounted to sample stage 52, including images of the test subject before, during and after mechanical indentation testing and video of the same.

Examples of nanomechanical test systems suitable to be configured for use with a tensile test holder according to embodiments of the present disclosure are described in U.S. Pat. Nos. 5,553,486 and 5,869,751, both of which are assigned to the same assignee as the present disclosure and incorporated herein by reference. Another test system suitable for configuration with the heater 100 is an electron microscopy (e.g. transmission electron and/or scanning electron) in-situ nanomechanical tester commercially available under the trade name PicoIndenter from Hysitron, Incorporated, of Minneapolis, Minn., USA.

During a temperature controlled mechanical testing, as will be described in greater detail below, heater 100 is controlled so as to heat and maintain the test subject 31 at the desired temperature. The heater 100 is operated with at least one of open loop control or closed loop control. For more accurate temperature regulation in a changing thermal environment, the closed loop control system utilizing the temperature signal 8 as the feedback is used. When the sample temperature reaches the desired temperature, EM transducer 32 is operated to apply a force with the moveable probe 34 to the test subject 31. According to one embodiment, the temperature of the test subject 31 is measured by the heater 100 (e.g., including a temperature sensor) and the force applied and a displacement of the indented material of the test subject 31 are measured by nanomechanical test system 30. The nanomechanical test system 30 measures these parameters through the actuator 36 and the displacement sensor 38 of EM transducer 32. These parameters are measured while being synchronously imaged, in one example, via imaging device 96 including for instance an electron microscope. In another example, in-situ imaging of the sample uses an indenter in a scanning probe microscope. The force and displacement data and images of the corresponding indentation are substantially simultaneously measured and observed by a combination of the actuator 36, the displacement sensor 38 and the imaging device 96 (e.g., an electron microscope). Stated another way, examination of the test subject—through the above described measuring and imaging techniques—at a specified testing temperature is thereby performed without any appreciable pause between measurement, imaging or heating. Phenomena including elastic deformation and the like that alter the shape of the indentation over time after application of the indentation force have minimal effect on the measurement and imaging of the indentation. Additionally, elastic deformation and the like are observable and measurable for a time period starting immediately after indentation. That is to say, because the nanomechanical test system 30 with the heater 100 is able to perform the indentation testing, and measure and observe the material surrounding the indentation at substantially the same time, changes in the material over a period of time are similarly observable at the time of and immediately after the indentation. Observation of these parameters and phenomena at or immediately after indentation are sometimes critical in the accurate assessment and determination of corresponding material properties.

Figure 2A:
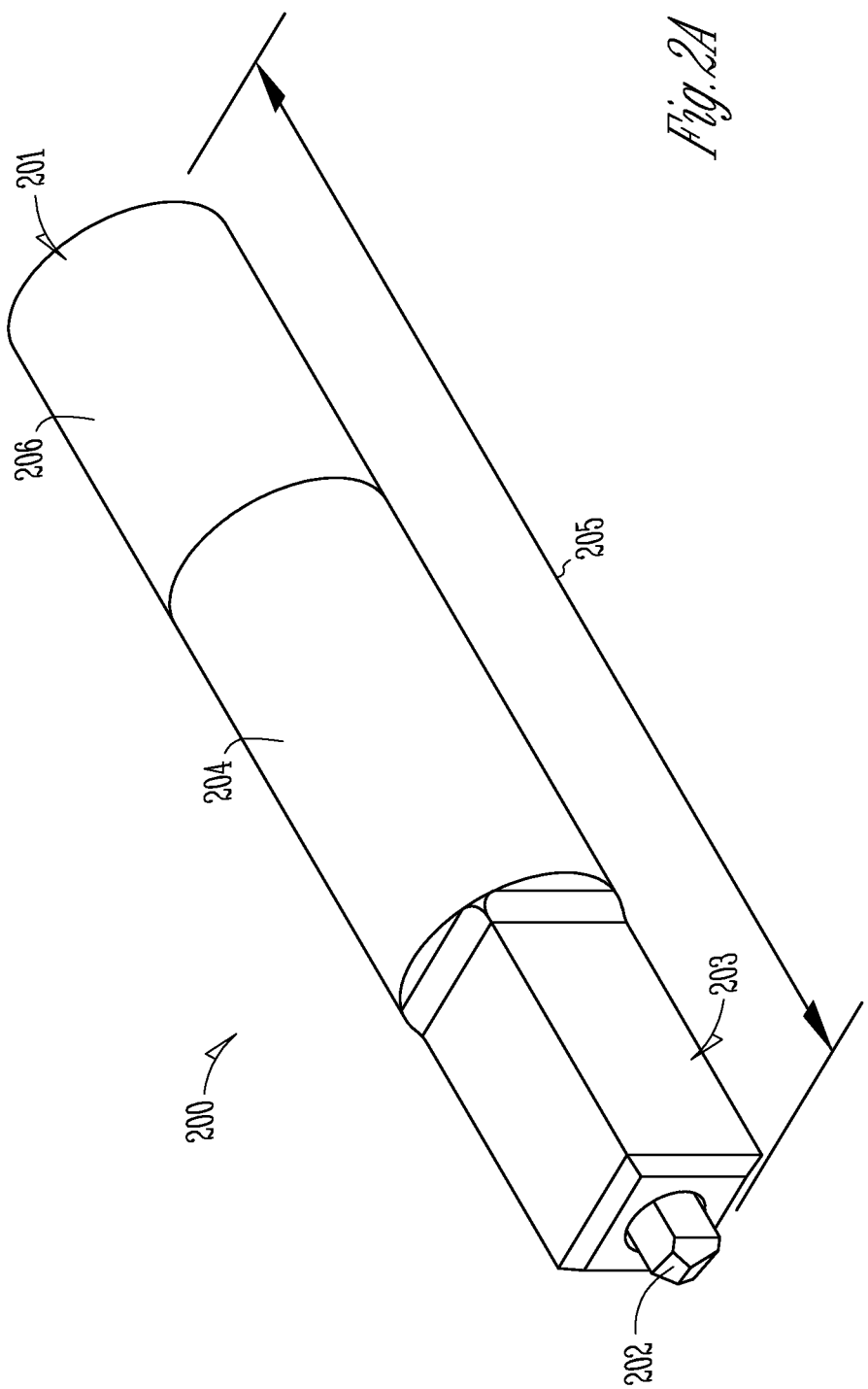
FIG. 2A is a perspective view of one example of an indentation assembly.

FIG. 2A shows one example of an indentation assembly 200 extending from an assembly proximal end 201 to an assembly distal end 203. The indentation assembly 200 includes an assembly length 205 from the proximal end 201 to the distal end 203. The indentation assembly 200 includes an indentation tip 202, a tip holder 204 and a tip holder mount 206. The indentation assembly 200 is configured for coupling with a transducer, for instance, a transducer used in submicron mechanical testing of heated test subjects. Although shown as an indentation assembly, the assembly 200 also includes, but is not limited to, scratching, compression, tensile, fracture assemblies and the like.

Referring now to FIGS. 2B and 2C the indentation assembly 200 is shown with the tip holder 204 receiving the indentation tip 202. Referring to FIG. 2B, the indentation tip 202 includes a tip barrel 210 received within a tip socket 208. The tip socket 208, in one example, includes sufficient space around the indentation tip 202 for the reception of adhesives including heat resistive epoxy adhesives configured to tightly retain the indentation tip 202 within the tip holder 204 across a wide range of temperatures, for instance, from 0 to 800° C.

The tip holder 204 further includes a mounting boss 212 sized and shaped for reception within a mounting socket on the tip holder mount 206. In one example, the mounting socket 214 is sized and shaped to interference fit with the mounting boss 212. In still another example, the mounting boss 212 is spaced from the wall defining the mounting socket 214 to facilitate the addition of adhesives such as heat resistant adhesives, as previously described, to fixedly couple the tip holder mount 206 with the tip holder 204. The tip holder mount 206 further includes a coupling feature 216. The coupling feature 216 is sized and shaped for a coupling with a transducer, for instance a transducer for submicron mechanical testing as previously described and shown in FIG. 1. In one example, the coupling feature 216 includes, but is not limited to, mechanical interfittings, threading, interference fittings and the like for removably coupling the indentation assembly 200 to the transducer. Optionally, the tip holder mount 206 is not included in the indentation assembly 200 and the tip holder 204 is directly coupled with the transducer 32. For example, the tip holder 204 is removably or non-removably engaged with the transducer 32. Stated another way, the transducer 32 includes a tip holder mount, and in a similar manner to that described herein the tip holder 204 includes a minimized thermal conductivity and coefficient of thermal expansion to throttle heat transfer to the transducer tip holder mount.

As will be described in further detail below, the indentation assembly 200 is constructed with one or more materials having minimal thermal conductivities and minimal coefficients of thermal expansion. The indentation tip 202, in one example, is constructed with, but not limited to, diamond, cubic boron nitride or sapphire. The tip holder 204, in another example, is constructed with a material including but not limited to ZeroDur® or Clearceram®. ZeroDur® is made by Schott AG and has a coefficient of thermal expansion from around $0\pm0.05\times10^{-6}$/K and a thermal conductivity of around 1.46 W/m*K. In another example, the tip holder 204 is constructed with Clearceram®. The Clearceram® tip holder 204 has a coefficient of thermal expansion around $2.0\times10^{-6}$/K. Additionally, Clearceram® has a thermal conductivity of 1.51 W/m*K. Each of these materials provides a low coefficient of thermal expansion and thermal conductivity to the tip holder 204. Heat transmitted to the tip holder 204, for instance, through the indentation tip 202 and the environment surrounding the indentation assembly 200 is throttled (e.g., impeded and minimized) as it passes through the tip holder 204 and moves toward the tip holder mount 206.

The tip holder mount 206 is also constructed with one or more materials having low coefficients of thermal expansion and low thermal conductivities. In one example, the tip holder mount 206 is constructed with a material including Invar, a nickel steel alloy notable for its low coefficient of thermal expansion and ease of manufacturing processing (e.g., forming coupling features such as threading, mechanical interfits and the like). Invar has a thermal conductivity between 12 and 15 W/m*K and a coefficient of thermal expansion in the range of 1.2 to $7.8 \times 10^{-6}$/K. In another example, the tip holder mount 206 is constructed with a material including Macor another machineable glass ceramic built and sold by Corning Inc. The thermal conductivity of Macor is 1.46 W/m*K and Macor has a coefficient of thermal expansion around 7.4 to $11.4 \times 10^{-6}$/K. In another example, the tip holder mount 206 has a lower thermal conductivity than the tip holder 204.

As shown, the tip holder mount 206 is constructed with materials having similar but slightly higher coefficients of thermal expansion and thermal conductivities relative to the materials used in the tip holder 204. The differing materials used in the tip holder mount 206 are more easily mechanically processed, for instance, to include coupling features 216, such as threading, mechanical interfits and the like, for coupling the indentation assembly 200 with the transducer. In contrast, the materials of the tip holder 204 having relatively reduced coefficients of thermal expansion and thermal conductivities are difficult to mechanically process with coupling features, such as the coupling feature 216 shown in FIG. 2B. Optionally, the indentation assembly 200 is constructed without the tip holder mount (e.g., the tip holder 204 forms the assembly) and the tip holder 204 is coupled with the transducer 32 shown in FIG. 1. Stated another way, the indentation assembly 200 is fixed (e.g., integral, fixed and the like) to the transducer 32 thereby eliminating the tip holder mount 206 otherwise used to exchange tips. In another option, the tip holder mount 206 is included in the transducer (e.g., integral) and the tip holder 204 is subsequently coupled with the mount 206.

The tip holder 204 forms the majority of the volume and length of the indentation assembly 200. Heat transmitted from the indentation tip 202 (e.g., upon engagement with a lower or higher temperature sample 31) and the surrounding environment to the indentation assembly 200 is transmitted first through the large volume and length of the tip holder 204 prior to any residual transmission of heat to the tip holder mount 206 and the transducer coupled thereto. By forcing heat transfer through the tip holder 204 thermal expansion and mechanical drift of the indentation assembly 200 are minimized in comparison to an indentation assembly 200 constructed with solely the materials found, for instance, in the tip holder mount 206. In another example, where the tip holder 204 is a substantial majority of the volume and length of the indentation assembly 200 relative to the tip holder mount 206, forcing heat transfer into the larger and longer tip holder 204 prior to heat transfer through the tip holder mount 206 enhances the throttling of heat through the indentation assembly 200. Stated another way, the length and the volume of the tip holder mount 206 are minimized so the majority of the material used in the indentation assembly 200 is in the tip holder 204.

By maximizing the volume and the length of the tip holder 204 the lower coefficients of thermal expansion and thermal conductivities of the tip holder 204 are thereby leveraged over a larger percentage of the indentation assembly 200 to enhance the throttling of heat transfer through the tip holder 204 to the components of the tip holder mount 206 and transducer coupled with tip holder mount. That is to say, where there is a limited amount of space between the transducer of the submicron mechanical testing assembly and a test subject, the tip holder 204 extends across the majority of the space between the subject and the submicron mechanical testing assembly to ensure heat transfer is effectively and primarily throttled by the tip holder 204 and the heat throttling materials of the tip holder as opposed to the tip holder mount 206. Referring again to FIG. 2B, the indentation assembly is shown extending the assembly length 205 with a corresponding assembly volume (a composite of the mount and holder volumes). The tip holder mount 206 extends a mount length 209 and has a mount volume, $V_M$. In contrast, the tip holder 204 extends a tip holder length 207 and has a corresponding tip holder volume $V_H$. The tip holder length 207 is greater than the mount length 209 and the tip holder volume $V_H$ is greater than the mount volume $V_M$. The tip holder 204 with the lower thermal conductivity and coefficient of thermal expansion relative to the mount 206 cooperates with the length 207 and corresponding holder volume (both relatively larger than that of the mount 206) to minimize both heat transfer to the tip holder mount 206 and expansion (or contraction) of the tip holder 204.

In operation, the indentation assembly 200 is coupled with a transducer (e.g., transducer 32 shown in FIG. 1). The transducer 32 actuates the indentation assembly 200 and indents (or laterally scratches) the indentation tip 202 into the sample 31. Upon engagement of the tip 202 with the sample 31 heat is transferred between the sample 31 and the tip 202 according to any temperature gradient therebetween. For instance, where the sample 31 is at a higher or lower temperature to the tip 202 heat is conducted into the tip 202 or drawn into the sample 31, respectively. The change in temperature of the indentation tip 202 causes expansion or contraction, respectively, that is minimized according to heat exchange constraint parameters including, but not limited to the minimal thermal conductivity and coefficient of thermal expansion of the tip holder 204 relative to the tip holder mount 206. As described above, the low thermal conductivity and coefficient of thermal expansion of the tip holder 204 through materials, such as Zerodur®, substantially minimizes expansion and contraction and thereby ensures the indentation tip 202 experiences little or no movement or drift (substantially no movement and substantially no drift) even with engagement with a sample 31 at higher or lower temperatures.

In another example, the indentation assembly 200 includes additional heat constraint parameters including the relative volumes $V_H$, $V_M$ of the tip holder 204 and the tip mount 206 and the relative lengths of the same (e.g., 207, 209). The tip holder 204, in one example, includes the lowest thermal conductivity and the lowest coefficient of thermal expansion. By maximizing the volume and length 207 of the tip holder 204 the holder is able to leverage the lower thermal conductivity and coefficient of thermal expansion to maximize the throttling of the heat transfer and thereby further minimize corresponding expansion or contraction. Stated another way, the tip holder 204 is the largest component (by volume and length) of the overall indentation assembly. Because the tip holder 204 has the lowest coefficient of thermal expansion and thermal conductivity the overall expansion and contraction of the assembly 200 is correspondingly minimized (e.g., with engagement against a sample, heating or cooling with a heat exchanger, radiation and convection from the surrounding environment and the like). Moreover, the heat exchange constraint parameters described herein also minimize the conduction of heat through the indentation assembly from the indentation tip 202 to, for instance, the transducer 32. The indentation assembly 200 thereby substantially ensures the transducer is not subject to undesirable heating or cooling and corresponding expansion and contraction. Alternatively, the tip holder 204 is not the largest or longest component of the indentation assembly. Instead the tip holder 204 is interposed between other components of the indentation assembly and thereby throttles heat transfer in to other components according to its minimal thermal conductivity and coefficient of thermal expansion.

FIGS. 3A and 3B show one example of the indentation tip 202 shown in FIGS. 2A and 2B. As shown, the indentation tip 202 extends along a tip barrel 210 to a faceted tip face 300. The tip face 300 includes two or more facets sized and shaped to create a pointed surface for indentation of subjects underlying the indentation tip. Although a three-faceted tip face 300 is shown in FIGS. 3A and 3B, in other examples the indentation tip 202 includes faceted tip faces having two or more facets. Optionally, the indentation tip 202 includes other shapes including, but not limited to, a cylinder, cone and the like with or without facets. As previously described, in one example, the indentation tip 202 is constructed with diamond.

One example of the tip holder 204 is shown in FIGS. 4A and 4B. As previously described, the tip holder 204 includes a tip socket 208 for reception of the indentation tip 202 and a mounting boss 212 for reception within the tip holder mount 206. Referring now to FIGS. 4A and 4B, the tip holder 204 includes a tip holder body 404 having a tip collar 400 extending around the tip socket 208. Referring to FIG. 4B, the tip holder 204 further includes a tip holder mount shelf 402 adjacent to the mounting boss 212. As will be described in further detail below, the mounting boss 212 and the tip holder mount shelf 402 cooperate to create a tight positive engagement with the tip holder mount 206. Forces incident on the tip holder mount 206 from the transducer are thereby fully transmitted through the tip holder 204 to the indentation tip 202 received within the tip socket 208 without relative movement therebetween. Although the tip barrel 400 is shown with a faceted columnar configuration, in another example, the tip collar 400 has a substantially isodiametric shape to the remainder of the tip holder body 404.

FIGS. 4C, 4D and 4E show additional views of the tip holder 204 including cross-sectional, front elevational and rear elevational views of the tip socket 208, mounting boss 212 and tip holder mounting shelf 402.

FIGS. 5A-E show one example of the tip holder mount 206. As previously described, the tip holder mount 206 includes a coupling feature 216 sized and shaped to removably couple the indentation assembly 200 with a submicron mechanical testing assembly including the transducer of the mechanical assembly. The tip holder mount 206 further includes the mounting socket 214 sized and shaped to receive the mounting boss 212 (see FIG. 2B) of the tip holder 204.

FIGS. 5A and 5B show opposed perspective views of the tip holder mount 206. Referring first to FIG. 5A, a bevel 500 is included with the mounting socket 214. The bevel 500 facilitates easy insertion of the mounting boss 212 into the mounting socket 214 while at the same time leaving a tip holder engagement surface 504 sized and shaped for flush engagement with the tip holder mounting shelf 402 shown in FIGS. 4B and 4E. Referring now to FIG. 5B, the coupling feature 216, for instance, an orifice within the tip holder mount 206, includes a similar bevel 502 sized and shaped to facilitate reception of the mounting post of the transducer within the tip holder mount 206. As previously described above, the tip holder mount 206 is constructed with materials having minimal coefficients of thermal expansion and thermal conductivities that at the same time are capable of mechanical processing to form the coupling feature 216. For instance, the couple feature 216 is machined out of the tip holder mount 206 to form one or more of threading, mechanical interfittings, interference fits and the like for coupling with the transducer of the submicron mechanical testing assembly.

Referring now to FIGS. 5C, 5D and 5E, additional views of the tip holder mount 206 are provided. For instance, referring to FIGS. 5C and 5D the tip holder mount 206 is shown with the tip holder engaging surface 504 and the bevel 500. As previously described above, the tip holder engaging surface 504 is sized and shaped to flushly engage with the corresponding tip holder mounting shelf 402 shown in FIGS. 4B and 4E. Similarly, FIGS. 5C and 5E show the coupling feature 216 including an orifice having features therein for coupling with the submicron mechanical testing assembly. The figures further show the bevel 502 sized and shaped to facilitate entry of a mounting post into the tip holder mount 206.

Referring now to FIG. 6A, another example of the indentation assembly 200 is shown positioned within a thermal shield 600. The thermal shield 600 includes a thermal shield body 601 surrounding an indenter socket 602. The indenter socket 602 is sized and shaped to receive at least the tip holder mount 206 as well as a portion of the tip holder 204. In another example, the indenter socket 602 is sized and shaped to receive only the tip holder mount 206. As shown, the shield body 601 substantially conceals the tip holder mount 206. By concealing the tip holder mount 206 the thermal shield 600 substantially isolates the tip holder mount 206 (physically and thermally) from the environment surrounding the indentation assembly 200. Optionally, the thermal shield 600 extends along the indentation assembly 200, for instance over the tip holder mount 206 and the tip holder 204 to isolate substantially all of the indentation assembly 200 from the surrounding environment.

In one example, where the thermal shield 600 is part of a heat exchanger assembly, inflow and outflow tubes 604, 606 are provided to transmit fluids (e.g., convective fluids for heating and cooling, such as refrigerants) into and out of the thermal shield 600. Fluids used with the thermal shield include, but are not limited to, chilled or heated water, glycol, ammonia, gases and the like. In another example, a gap extends between the thermal shield 600, the tip holder mount 206 and the tip holder 204 to substantially prevent physical engagement between the indentation assembly 200 and the thermal shield. The indentation assembly 200 is thereby substantially isolated from mechanical vibration, for instance from the flow of heating or cooling fluids through the thermal shield 600. Optionally, the thermal shield 600 includes one or more of the heat exchangers described herein (e.g., a resistive heater, Peltier heat exchanger and the like).

In another example, the thermal shield 600 includes a temperature sensor 603 including, but not limited to, a thermometer, thermocouple, resistive temperature measuring sensor and the like. The temperature sensor 603 is configured to measure the temperature of the indentation tip 202 (or another component of the indentation assembly 200 adjacent to the tip). Further, where the thermal shield 600 acts as a heat exchanger, the temperature sensor 603 cooperates with the heat exchanger to precisely control the temperature of the indentation tip 202 (e.g., through closed loop control). In still another example, the temperature sensor 603 is included in one or more of the remainder of the indentation assembly 200 or any of the heat exchangers described herein and is configured for measuring the temperature of one or more of the indentation tip 202 and other components of the indentation assembly 200. Optionally, the temperature sensor 603 is configured to measure temperatures from around −20 degrees Celsius or lower to around 1000 degrees Celsius or more (e.g., corresponding to the range of tip temperatures available with the heat exchangers described herein).

The indentation assembly 200 in combination with the thermal shield 600 is configured to position the tip holder mount 206 in isolation relative to the exterior environment. As previously described, the tip holder mount has a relatively higher thermal conductivity and coefficient of thermal expansion relative to the tip holder 204. Because the tip holder mount 206 has the increased properties relative to the tip holder 204 thermal isolation of the tip holder mount 206 with the thermal shield assists in minimizing any undesirable mechanical drift or thermal expansion caused by heat energy passing from the environment surrounding the indentation assembly 200, for instance by convection and radiation. In another example, the thermal shield 600 minimizes the thermal expansion and mechanical drift of the tip holder mount 206 through conduction of residual heat from the tip holder 204.

Because the tip holder 204 has a generous length relative to the tip holder mount 206 (for instance, in the space between transducer and the subject), the tip holder mount 206 is correspondingly limited to a much smaller length relative to the tip holder. In combination with the heat throttling benefits of the tip holder 204, as shown in FIG. 6A, the thermal shield 600 extends fully or near fully around and along the shorter tip holder mount 206 and effectively shields the tip holder mount from convection and radiation heat transfer. In another example, the thermal shield cools the entirety of the tip holder mount 206 to substantially retard any thermal expansion and mechanical drift of the tip holder mount 206 caused by conduction from the tip holder 204. The indentation assembly 200 is thereby maintained in a substantially unexpanded and static state when subjected to heat from a test subject, for instance, a test subject heated with a heater 100 (FIG. 1) or heat from the environment surrounding the indentation assembly 200.

FIG. 6B shows another example of an indentation assembly 200 including a heat exchanger 608. As shown, the indentation assembly 200 includes an indentation tip 202 positioned within and coupled with a tip holder 204. The tip holder 204 is coupled with a tip holder mount 206. The indentation assembly 200 is constructed with similar materials to the previously described indentation assembly 200 including materials within the tip holder 204 and the tip holder mount 206 having minimal coefficients of thermal expansion and thermal conductivities. As shown in FIG. 6B, the heat exchanger 608 is positioned adjacent to and surrounding the indentation tip 202. The heat exchanger 608 is thereby configured to locally heat or cool the indentation tip 202 without otherwise heating or cooling the remainder of the indentation assembly 200, for instance, the proximal portions of the tip holder 204 and the tip holder mount 206. In another example, the heat exchanger 608 is positioned similarly to the heat shield of FIG. 6A, for instance, the heat exchanger 608 is positioned around the tip holder mount 206 and a portion of the tip holder 204. In the example shown in FIG. 6B, the heat exchanger 608 is positioned adjacent to the indentation tip 202.

By localizing heat exchange to the indentation tip 202 heat transferred to the remainder of the tip holder 204 and the tip holder mount 206 is substantially minimized. By minimizing the heat exchange to the remainder of the tip holder 204 and the tip holder mount 206 expansion due to heat exchange is substantially minimized. For instance, as previously described above, the tip holder 204 and the tip holder mount 206 are constructed with the materials having minimal thermal conductivities and coefficients of thermal expansion. By localizing the heat exchange 608 to the portion of the tip holder 204 adjacent to the indentation tip 202 heat transfer is throttled to the remainder of the indentation assembly 200 (e.g., the proximal portion of the tip holder 204 and the tip holder mount 206) thereby minimizing any expansion and corresponding mechanical drift of the indentation assembly 200 caused by changes in dimensions of the tip holder 204 and tip holder mount 206.

Referring again to FIG. 6B, the heat exchanger 608 in one example is a resistive heat exchanger having one or more resistive elements positioned around at least a portion of the indentation tip 202. As shown in FIG. 6B, leads 610 extend through the tip holder mount 206 and the tip holder 204 to electrically couple with the heat exchanger 608. Terminals 612 are further provided at the tip holder mount 206 for coupling with corresponding terminals on a transducer body. In yet another example, the heat exchanger 608 includes a temperature sensor 603 positioned therein to facilitate the measurement of the temperature of the indentation tip 202, for instance, during heating of the heat exchanger 608. Optionally, the temperature sensor makes use of the leads 610. In another option, the temperature sensor includes leads and corresponding terminals of its own configured for coupling with corresponding terminals in the transducer body housing the indentation assembly 200. In yet another example, the heat exchanger 608 is a fluid heat exchanger and the leads 610 corresponding to fluid conduits sized and shaped to direct fluids such as chilled or heated water, ammonia or the like to the heat exchanger 608 for heating and cooling of the indentation tip 202.

FIG. 6C shows another example of the indentation assembly 200 including a Peltier heat exchanger 614. In a similar manner to the heat exchanger 608 shown in FIG. 6B the Peltier heat exchanger 614 is, in one example, an electrically operated heat exchanger positioned near the indentation tip 202. As shown in FIG. 6C, leads 620 extend from terminal 622 at the tip holder mount 206. The lead 620 are coupled with the Peltier heat exchanger 614, for instance, at one or more P-type elements 616 and N-type elements 618. The P-type element 616 corresponds to positively doped elements or semi-conductors positioned around at least a portion of the indentation tip 202. In a similar manner, the N-type element 618 correspond to a negatively doped semi-conductors positioned around the indentation tip 202. Current delivered through the lead 620 and the P-type and N-type elements 616, 618 selectively heats and cools the indentation tip 202. In one example, multiple layers 617, 619 are positioned around the indentation tip 202 to enhance the heat exchange capabilities of the Peltier heat exchanger 614. That is to say, the P-type and N-type elements 616, 618 are arranged in layers 617, 619 to provide staged heat exchange to the indentation tip 202. In other example, multiple layers including first, second and third layers of P-type and N-type elements 616, 618 are provided to further enhance the heat exchange capabilities of the Peltier heat exchanger 614.

In a similar manner to the heat exchanger 608 shown in FIG. 6B, the Peltier heat exchanger 614 is also positionable at a proximal portion of the indentation assembly 200, for instance, around or at the tip holder mount 206 and a portion of the tip holder 204. Because of the minimal thermal conductivities and coefficients of thermal expansion of each of the tip holder 204 and the tip holder mount 206 the indentation assembly 200 experiences minimal thermal expansion due to heating or cooling of the indentation assembly through the Peltier heat exchanger 614. Further, the minimal thermal conductivity substantially prevents the transmission of heat energy (e.g., cooling or heating) to the transducer coupled with the indentation assembly 200.

In all of the heat exchangers described herein, a temperature sensor 603 is optionally included. The temperature sensor 603 facilitates control of the heat exchangers, for instance with closed loop control (and heater control circuit 4 and heating module 58 in FIG. 1) to raise and lower the temperature of the indentation tip 202 as desired. In one example, the heater control circuit 4 raises and lowers the temperature of one or more of the indentation tip 202 to correspond with the temperature of the test sample 31 or sample stage 52 (e.g. a sample temperature). By corresponding (e.g., substantially matching) the temperature of the indentation tip 202 to the sample temperature heat transfer and corresponding (difficult to predict) expansion or contraction of the indentation assembly 200 are substantially minimized. Similarly, drift of the indentation tip 202 and according error in measurements taken with the tip 202 (at least until equalization of temperatures through conduction where the tip 202 is engaged with the sample) are correspondingly minimized. Stated another way, the indentation assemblies 200 with the heat exchangers described herein are configured to immediately indent (or scratch, abrade and the like) with the tip 202 at substantially the same temperature as the sample 31 without undesirable expansion and drift of the tip 202 through heat transfer caused by temperature gradients. Accurate and reliable measurements are thereby immediately obtained with the indentation assemblies 200 without delays for temperature equalization. Referring now to FIGS. 7A and 7B, another example of an indentation assembly 700 is shown. The indentation assembly 700 includes a tip holder 702 including an integral tip holder mount 708. The tip holder 702 (including the tip holder mount) includes but is not limited to tip holders constructed with Zerodur® Macor, Invar and the like. As previously described, constructing the tip holder 702 with these materials substantially throttles heat transfer from the indentation tip 704 through the tip holder 702 and to the interface with a transducer coupled at the tip holder mount 708.

As shown in FIGS. 7A and 7B, the indentation assembly 700 further includes a fitting 710 positioned within the tip holder mount 708. As shown, the fitting 710 includes an orifice 712 sized and shaped to receive a corresponding post from the transducer. In one example, the fitting 710 is constructed with a machineable material including, but not limited to, brass. The fitting 710 is mechanically processed to form coupling features such as mechanical interfits, interference fits, threading and the like. The fitting 710 thereby acts as an intermediate between the tip holder 702 and the transducer to facilitate the removable coupling of the indentation assembly 700 with the transducer. Where the tip holder 702 is constructed with a material that is difficult to mechanically process and form coupling features, the fitting 710 includes a material that is capable of both mechanical processing and bonding to the tip holder 702 (e.g., through the tip holder mount 708). Stated another way, the fitting 710 is interposed between the transducer and the tip holder 702 to facilitate coupling between the tip holder 702 that is difficult to mechanically process and the transducer. As shown in FIGS. 7A, B the tip holder mount 708 is constructed with the same material (e.g., Zerodur, Clearceram and the like) as the tip holder 702. The indentation assembly 700 thereby includes a minimized thermal conductivity and a minimized coefficient of thermal expansion.

In yet another example of an indentation assembly, the indentation assembly includes coupling a diamond indentation tip with a glass shank. The glass shank and the indentation tip are coupled with, but not limited to, heat resistant adhesives, mechanical fittings, interference fitting and the like. The glass shank is then attached to the tip holder. In one example, the glass shank is adhered to the tip holder, for instance, with a heat resistant epoxy cement or mechanical coupling (e.g., the fittings as described above, including threading).

FIG. 8 shows another example of an indentation assembly 800. In a similar manner to the previously described indentation assembly 200 the indentation assembly 800 includes an indentation tip 202 coupled with a tip holder 804, the tip holder 804 is in turn coupled with a tip holder mount 806. In the example shown in FIG. 8, a tip fitting 810 is interposed between the indentation tip 202 and the tip holder 804. For instance, the tip fitting 810 is positioned within a fitting recess 812 of the tip holder 804. In one example the tip fitting 810 is constructed with a material such as Invar®. The tip fitting 810 is constructed with Invar® which includes a minimal thermal conductivity and coefficient of thermal expansion to facilitate the machining of the tip fitting 810 for interposing between the indentation tip 202 and the tip holder 804 within the fitting recess 812.

The tip fitting 810 provides a snug structural fitting between the indentation tip 202 and the tip holder 804. The snug fit between the indentation tip 202 and the tip holder 804 aligns the indentation tip 202 with the longitudinal axis of the tip holder 804 and thereby minimizes the adhesive needed to hold the indentation tip 202 therein. Stated another way, adhesive within the fitting recess 812 is not relied upon for alignment and structural stabilizing of the indentation tip 202 relative to the tip holder 804. Instead, the indentation tip 202 is housed within the tip fitting 810 and the tip fitting 810 having a close shape to the inner perimeter of the fitting recess 812 engages with the tip holder 804 and thereby automatically aligns and structurally supports the indentation tip 202 therein. Optionally, adhesive is applied between the tip fitting 810 and the inner surface of the tip holder 804 within the fitting recess 812 to affix the indentation tip 202 and the tip fitting 810 therein. In one example, the indentation tip 202 is coupled with a tip fitting 810 having a inner perimeter sized and shaped (e.g., uniquely machined) to the unique dimensions of the indentation tip 202. The indentation tip 202 is thereafter adhered within the tip fitting 810 to form an assembly for ready coupling with the tip holder 804. The use of the tip fitting 810, for instance, with the adjustable fitting thickness 814 (machined according to the relative dimensions between the indentation tip 202 and the set diameter of the fitting recess 812 thereby provides a reliable structural support configured to snuggly engage the indentation tip 202 with the tip holder 804 irrespective of the unique dimensions of the indentation tip 202 relative to the fitting recess 812.

The tip holder mount 806 shown in FIG. 8, is configured for reception within a mount recess 816 formed in the tip holder 804. As shown in FIG. 8, the mount recess 816 is sized and shaped to receive the tip holder mount 806 therein. As with previously described examples, the tip holder mount 806 includes a coupling feature 818, for instance, a threaded opening sized and shaped for coupling with the transducer such as the transducer 32 shown in FIG. 1. As shown in FIG. 8, the tip holder 804 substantially surrounds the tip holder mount 806 when the tip holder mount 806 is positioned within the mount recess 816. As previously described, in one example, the tip holder 804 is constructed with a material having a minimal coefficient thermal expansion and thermal conductivity relative to the material in the tip holder mount 806. For instance, in one example, the tip holder 804 is constructed with but not limited to Zerodur while the tip holder mount 806 is constructed with easily machineable materials such as Invar®. As previously described, Invar® 806 while having a slightly higher coefficient of thermal expansion and thermal conductivity Zerodur still has a minimal coefficient of thermal expansion and thermal conductivity. As shown in FIG. 8, the tip holder 804 constructed with the material having a lesser coefficient thermal expansion and thermal conductivity relative to that of tip holder mount 806 extends around the tip holder mount 806 and thereby maximizes the volume and length of the tip holder 804 relative to the tip holder mount 806. By maximizing the volume and length of the tip holder 804 relative to the tip holder mount 806 the coefficient of thermal expansion and the thermal conductivity of the tip holder 804 is leveraged relative to the higher coefficient of thermal expansion and thermal conductivity of the tip holder mount 806. Stated another way by minimizing the volume and length of the tip holder mount 806 any expansion and conduction of heat energy through the indentation assembly 800 is substantially minimized relative to other embodiments where the tip holder mount 806 may assume more length or volume of the overall indentation assembly 800.

FIG. 9 shows another example of an indentation assembly 900. The indentation assembly 900 includes an indentation tip 202 coupled with a tip holder mount 906 with a tip holder 904 therebetween. As described above, in one example, the tip holder 904 is constructed with a material configured to throttle heat transfer and minimize expansion and contraction of the indentation assembly 900 through changes in temperature. For instance, the tip holder 904 is constructed with Zerodur®. In another example, the tip holder mount 906 is constructed with another material capable of shaping, machining and the like for coupling with a transducer (e.g., by threading, mechanical fitting and the like). For instance, the tip holder mount 906 is constructed with Invar having a minimal thermal conductivity and coefficient of thermal expansion (but higher than that of the tip holder 904). In yet another example, the indentation assembly 900 includes an optional feature 908 interposed between the tip holder mount 906 and the tip holder 904. The feature 908 includes, but is not limited to, an intervening structural component that transmits forces between the indentation tip 202 and the transducer, a heat exchanger, instrument and the like.

In contrast to the previously described examples, the tip holder 904 is not the largest or longest portion of the indentation assembly 900. Referring to FIG. 9, the indentation assembly 900 has an assembly length 907 and the tip holder 904 and the tip holder mount 906 have lengths 907, 909, respectively, with the length 907 of the holder 904 being close or shorter to the length 900 of the mount 906. Similarly, the volume of the tip holder 904, in at least one example, is less than that of the tip holder mount 906. The tip holder 904 of the indentation assembly 900 relies on its minimal thermal conductivity to throttle heat transfer into the other components of the assembly 900. By throttling the heat transfer the tip holder mount 906 (and feature 908 where included) experience little or no change in temperature when the indentation tip 202 is heated or cooled. The tip holder mount 906 thereby expands or contracts minimally because of the thermal isolation provided by the tip holder 904. Further, the minimal coefficient of thermal expansion of the tip holder 904 ensures the tip holder experiences minimal expansion or contraction through temperature changes. Stated another way, the tip holder 904 provides a thermal break in the indentation assembly 900 that isolates the indentation tip 202 (whether actively heated or cooled by a heat exchanger or contact with a sample) from the other components including the tip holder mount 906. Further, the tip holder 904 isolates the transducer coupled with the indentation assembly 900 from the heated or cooled indentation tip. Expansion, contraction and the like of the indentation assembly 900 and the transducer coupled with the assembly are thereby minimized.

In another example, the indentation assembly 900 includes one or more of the heat exchangers 608, 614, temperature sensors 603 and thermal shields 600 described herein. The heat exchangers, 608, 614, in one example, are positioned adjacent to the tip holder 904 and the indentation tip 202 to selectively heat and cool the indentation tip 202 as needed for mechanical testing. The tip holder 904 substantially ensures heat or cooling at the tip (e.g., through engagement with a sample) or in the tip holder 904 through operation of the heat exchangers 608, 614 is isolated to the tip holder 904 portion of the indentation assembly 900. Expansion and contraction of other components of the assembly 900 (such as the tip holder mount 906) or a transducer coupled with the assembly are substantially avoided.

Conclusion

The indenter assemblies described herein provide holders capable of retaining an indenter tip while substantially minimizing both thermal expansion of the holder and heat transfer to an adjacent transducer. The tip holder is constructed with a material having minimal thermal conductivity and coefficient of thermal expansion. The tip holder mount is similarly constructed with a material having minimal thermal conductivity and a low coefficient of thermal expansion. In one example, the tip holder mount does not have a thermal conductivity and coefficient of thermal expansion as low as the tip holder. Instead, the tip holder mount is constructed with a material that is easily processed (e.g., machined) to form a coupling feature, such as threading, for coupling with the transducer of a sub-micron mechanical test assembly. The tip holder mount is thereby an intermediate feature between the tip holder and the transducer that facilitates the use of the tip holder material—in some examples a difficult to process material—for the majority of the indenter assembly while allowing for easy coupling with the transducer.

The tip holder relative to the tip holder mount is the majority (e.g., by volume and length) of the indenter assembly. Additionally, the tip holder is interposed between the indentation tip and the tip holder mount. The tip holder thereby primarily throttles heat from the indention tip and surrounding environment before any residual heat is transferred to the tip holder mount coupled with a transducer. Stated another way, the tip holder has substantially more volume than the tip holder mount, and the volume of the tip holder—with the attendant minimal thermal conductivity and coefficient of thermal expansion—effectively throttles heat transfer and ensures the tip holder mount—with minimal but larger thermal conductivity and coefficient of thermal expansion—is thermally isolated from heat transfer. Further, because the tip holder is longer than the tip holder mount, the tip holder positions the tip holder mount and a transducer coupled thereon further away from a heated test subject and the surrounding heated environment. The relatively large length of the tip holder compared to the tip holder mount correspondingly throttles heat transfer along the entire length of the tip holder and further retards heat transfer into the tip holder mount and the transducer. In contrast, using a shorter tip holder (in the space between the transducer and a heated subject) positions the transducer and any intermediate components in closer proximity to the heat source and reduces the heat throttling effectiveness of the tip holder.

Moreover, the indenter assembly is configured to position the tip holder mount (with the relatively higher thermal conductivity and coefficient of thermal expansion) in isolation within a thermal shield. Stated another way, because the tip holder mount has, in some examples, a higher thermal conductivity and coefficient of thermal expansion relative to the tip holder, thermal isolation of the tip holder mount minimizes any mechanical drift or thermal expansion caused by convection or radiation from the surrounding environment. In another example the thermal shield ensures the minimal heat energy conducted from the tip holder is absorbed by the shield to prevent thermal expansion and drift of the tip holder mount. The generous length of the tip holder relative to the tip holder mount within the space between the transducer and the test subject correspondingly limits the length of the tip holder mount to a value much less than the tip holder. The thermal shield extends fully or near fully around and along the shorter tip holder mount and effectively shields the entirety of the tip holder mount from convective and radiative heat transfer (and in some examples, from conductive heat transfer).

Although the present disclosure has been described in reference to preferred embodiments, persons skilled in the art will recognize that changes may be made in form and detail without departing from the spirit and scope of the disclosure. It is to be understood that the above description is intended to be illustrative, and not restrictive. Many other embodiments will be apparent to those of skill in the art upon reading and understanding the above description. It should be noted that embodiments discussed in different portions of the description or referred to in different drawings can be combined to form additional embodiments of the present application. The scope of the disclosure should, therefore, be determined with reference to the appended claims, along with the full scope of equivalents to which such claims are entitled.

What is claimed is:

1. An indentation assembly for nano and micron scale testing comprising:
    an indentation tip;
    a tip holder coupled with the indentation tip, the tip holder having a tip holder thermal conductivity and a tip holder coefficient of thermal expansion, and the tip holder includes a tip holder length and a tip holder volume;
    a tip holder mount coupled with the tip holder, the tip holder mount is configured for coupling with a transducer, the tip holder mount has a mount thermal conductivity greater than or equal to the tip holder thermal conductivity, the tip holder mount has a mount coefficient of thermal expansion greater than or equal to the tip holder coefficient of thermal expansion, and the tip holder mount includes a mount length and a mount volume; and
    the indentation assembly is configured to throttle heat transfer from the indentation tip to the tip holder mount, and the indentation assembly is configured to minimize expansion and contraction of the indentation assembly according to the thermal conductivity and coefficient of thermal expansion of the tip holder relative to the tip holder mount wherein:
        the tip holder length is greater than the mount length, and the indentation tip is spaced from the tip holder mount by the tip holder length, and
        the tip holder volume is greater than the mount volume.

2. The indentation assembly of claim 1, wherein the tip holder mount includes a mechanical fastener configured to couple with a transducer.

3. The indentation assembly of claim 1, wherein the tip holder consists of one or more of Zerodur® and Clearceram®.

4. The indentation assembly of claim 1, wherein the tip holder mount consists of one or more of Invar or Macor.

5. The indentation assembly of claim 1, wherein the tip holder thermal conductivity is around 1.46 W/m*K and the tip holder coefficient of thermal expansion is around $0\pm0.05\times10^{-6}$/K.

6. The indentation assembly of claim 5, wherein the mount thermal conductivity is around 12 and 15 W/m*K and the mount coefficient of thermal expansion is around $1.2$ to $7.8\times10^{-6}$/K.

7. The indentation assembly of claim 1 comprising a thermal shield extending around the tip holder mount, the thermal shield extends from the tip holder to the coupling feature, and the thermal shield isolates the tip holder mount from an environment exterior to the tip holder and the thermal shield.

8. The indentation assembly of claim 7, wherein an inner surface of the thermal shield is spaced from an outer surface of the tip holder mount.

9. The indentation assembly of claim 1 comprising a heat exchanger positioned adjacent to the indentation tip.

10. The indentation assembly of claim 9, wherein the heat exchanger consists of one or more of: a resistive heating element, a Peltier thermoelectric heat exchanger, and a fluid heat exchanger.

11. The indentation assembly of claim 1 comprising a tip fitting interposed between the tip holder and the indentation tip, the tip fitting aligns the indentation tip with the tip holder.

12. The indentation assembly of claim 1, wherein the tip holder mount is received within a mount recess in the tip holder.

13. A method of selectively heating an indentation assembly comprising:
    determining a sample temperature of one or more of a sample or a sample stage underlying the sample;
    determining a tip temperature of an indentation tip; and
    corresponding the tip temperature to the sample temperature including:
        directing heat transfer between a heat exchanger and the indentation tip, and
        throttling heat transfer from the heat exchanger toward a transducer coupled with the indentation assembly.

14. The method of claim 13, wherein corresponding the tip temperature to the sample temperature includes one or more of raising or lowering the tip temperature to substantially the sample temperature.

15. The method of claim 13, wherein directing heat transfer includes operating the heat exchanger adjacent to the indentation tip.

16. The method of claim 13, wherein directing heat transfer includes operating the heat exchanger remote from the indentation tip and near a tip holder mount.

17. The method of claim 13, wherein throttling heat transfer includes throttling heat transfer through a tip holder, the tip holder is coupled with a tip holder mount.

18. The method of claim 17, wherein throttling heat transfer through the tip holder includes throttling heat transfer according to heat exchange constraint parameters:
    a tip holder thermal conductivity and a tip holder coefficient of thermal expansion of the tip holder that are lower than a mount thermal conductivity and a mount coefficient of thermal expansion of the tip holder mount,
    a tip holder length of the tip holder is greater than a mount length of the tip holder mount, and the indentation tip is remotely positioned from the tip holder mount according to the tip holder length, and
    a tip holder volume of the tip holder is greater than a mount volume of the tip holder mount.

19. The method of claim 13, wherein determining the tip temperature of the indentation tip includes determining the tip temperature with a temperature sensor within the indentation assembly.

20. The method of claim 13, wherein determining the sample temperature includes determining the sample temperature with a temperature sensor within the sample stage.

21. The method of claim 13, comprising thermally isolating at least a portion of a tip holder and a tip holder mount with a thermal shield coupled around the indentation assembly.

22. A method for throttling heat transfer within an indentation assembly comprising:
   interposing a tip holder between a tip holder mount and an indentation tip, wherein the tip holder includes heat exchange constraint parameters including:
      a tip holder thermal conductivity and a tip holder coefficient of thermal expansion lower than a mount thermal conductivity and a mount coefficient of thermal expansion of the tip holder mount,
      a tip holder length greater than a mount length of the tip holder mount, and the indentation tip is remotely positioned from the tip holder mount according to the tip holder length, and
      a tip holder volume greater than a mount volume of the tip holder mount;
   retaining heat within the indentation assembly at an assembly proximal end according to the heat exchange constraint parameters, the assembly proximal end including the indentation tip and a proximal portion of the tip holder; and
   throttling heat transfer from the assembly proximal end toward the assembly distal end and the tip holder mount according to the heat exchange constraint parameters.

23. The method of claim 22 comprising changing an indentation tip temperature through engagement of the indentation tip with a sample having a sample temperature different than the indentation tip temperature.

24. The method of claim 22 comprising changing the indentation tip temperature with a heat exchanger coupled with the indentation assembly.

25. The method of claim 24, wherein changing the indentation tip temperature includes substantially matching a sample temperature, the sample temperature includes one or more of a temperature of the sample and a sample stage temperature.

26. The method of claim 24, wherein changing the indentation tip temperature with the heat exchanger includes operating the heat exchanger adjacent to the indentation tip.

27. The method of claim 22 comprising determining a tip temperature of the indentation tip with a temperature sensor within the indentation assembly.

28. The method of claim 22, comprising thermally isolating at least a portion of a tip holder and a tip holder mount with a thermal shield coupled around the indentation assembly.

* * * * *